United States Patent
McNeil (10) Patent No.: US 8,057,443 B2
(45) Date of Patent: Nov. 15, 2011

(54) APPARATUS FOR PROVIDING A FLUID PASSAGEWAY INTO AN INDIVIDUAL AND METHOD OF USE THEREOF

(75) Inventor: Iain D. McNeil, North Somerset (GB)

(73) Assignee: Medical Device Innovations Ltd., Halton (GB)

( * ) Notice: Subject to any disclaimer, the term of this patent is extended or adjusted under 35 U.S.C. 154(b) by 44 days.

(21) Appl. No.: 11/816,907

(22) PCT Filed: Feb. 23, 2006

(86) PCT No.: PCT/GB2006/000626
§ 371 (c)(1),
(2), (4) Date: Jul. 3, 2008

(87) PCT Pub. No.: WO2006/090148
PCT Pub. Date: Aug. 31, 2006

(65) Prior Publication Data
US 2008/0312638 A1    Dec. 18, 2008

(30) Foreign Application Priority Data
Feb. 23, 2005 (GB) .................................. 0503730.4

(51) Int. Cl.
*A61M 5/00* (2006.01)
(52) U.S. Cl. ........................................ 604/248; 604/513
(58) Field of Classification Search .................. 604/246, 604/248, 247; 600/564, 567
See application file for complete search history.

(56) References Cited

U.S. PATENT DOCUMENTS

| 3,057,350 | A | * | 10/1962 | Cowley .......................... 604/248 |
| 5,019,059 | A | * | 5/1991 | Goldberg et al. ............. 604/317 |
| 5,336,195 | A |   | 8/1994 | Daneshvar et al. ............ 604/179 |
| 5,376,071 | A | * | 12/1994 | Henderson .................... 604/115 |
| 5,527,276 | A | * | 6/1996 | Bruce ............................ 604/506 |
| 7,144,385 | B2 | * | 12/2006 | Matsuura et al. .............. 604/132 |
| 2002/0052564 | A1 | * | 5/2002 | Burbank et al. ............... 600/567 |
| 2004/0044306 | A1 | * | 3/2004 | Lynch et al. ................ 604/93.01 |

FOREIGN PATENT DOCUMENTS

EM    000545546-0001    7/2006

(Continued)

OTHER PUBLICATIONS

International Preliminary Report on Patentability for International Application No. PCT/GB2006/000626 dated Jan. 22, 2007.

(Continued)

*Primary Examiner* — Kevin C Sirmons
*Assistant Examiner* — Brandy C Scott
(74) *Attorney, Agent, or Firm* — Marshall, Gerstein & Borun LLP (57) ABSTRACT

Apparatus for the aspiration of a fluid from an individual, the apparatus comprising a port in fluid communication with the atmosphere; a catheter having a proximal end arranged to be inserted into the body of an individual and having a distal end; a one-way valve; and a fluid passage switch reversibly movable between a first position in which the distal end of the catheter is in fluid communication with the port and a second position in which the distal end of the catheter is in fluid communication with the one-way valve, the one-way valve being arranged to permit fluid flow there through in a direction from the distal end of the catheter. The apparatus may be used for both the aspiration of fluid from within the body and instillation of fluid into the body.

28 Claims, 9 Drawing Sheets

FOREIGN PATENT DOCUMENTS

| | | |
|---|---|---|
| EM | 000545546-0002 | 7/2006 |
| EP | 0 943 356 | 9/1999 |
| EP | 943356 A2 * | 9/1999 |
| JP | 62-84435 S | 5/1987 |
| JP | 08-196621 H | 8/1996 |
| JP | 11-4885 H | 12/1999 |
| JP | 2001-511399 | 8/2001 |
| JP | 2002-248164 | 9/2002 |
| JP | 2003-526398 | 9/2003 |
| WO | WO 93/00943 | 1/1993 |
| WO | WO 99/55407 | 11/1999 |

OTHER PUBLICATIONS

International Search Report for International Application No. PCT/GB2006/000626 dated Apr. 12, 2006.
Written Opinion of the International Searching Authority for International Application No. PCT/GB2006/000626.
Notice of Reasons for Refusal—Japanese Patent Application No. 2007-556656 mailed Jul. 27, 2010.
Decision of Refusal in JP Application No. 2007-556656, Dispatch No. 157291, Mar. 8, 2011, 8 pages.

* cited by examiner

APPARATUS FOR PROVIDING A FLUID PASSAGEWAY INTO AN INDIVIDUAL AND METHOD OF USE THEREOF

In a medical context aspiration is the process of relieving the build-up of unwanted fluid from within a patient's body. An example of a condition that is treated by aspiration is tension pneumothorax. A tension pneumothorax is a life-threatening condition that will lead to cardiac arrest and death if not treated expeditiously. Tension pneumothorax arises when air escapes from a damaged lung through a virtual one-way flap valve caused by damaged lung tissue. The nature of the lung damage allows air to escape from within the lung on inspiration (breathing in) into the chest cavity. On expiration (breathing out) the air within the chest cavity is unable to return into the lung and be expired, because the flap valve obstructs the flow of air back into the lung. As a result, the air pressure within the chest cavity increases with each breath. As the pressure arises, the lung is compressed and air entry into the lung becomes more difficult. Further increases in pressure cause the lung to become fully compressed and air entry becomes impossible. The air pressure on the damaged side may be sufficient to press against the mediastinum, containing the heart and the great vessels in the centre of the chest, compressing it and compromising heart function and circulation. Additionally, as this occurs, the other undamaged lung can become compressed, compromising its function also.

All of these factors inhibit the ability of the lungs to oxygenate the blood and the heart to pump. As a result, oxygen levels drop and brain function is reduced. As the pressure compromises oxygenation, lung and heart function, the normal compensatory mechanisms quickly fail and cardiac arrest and death will occur.

For effective treatment of tension pneumothorax, the pressure in the chest cavity must be released. This is traditionally done, in the pre-hospital emergency area, by placing a wide-bore needle and plastic cannula into the chest cavity and releasing the pressure. This is effective, but in itself compromises lung function as an open passage is left in the chest wall which effects lung function. Safely securing such a device is very difficult and it can become dislodged obviating its benefit. In addition, medical practitioners may not realise the device has become dislodged.

Other examples of conditions in which aspiration is required for relief of that condition include cardiac tamponade, which is the compression of the heart caused by blood or fluid accumulation in the space between the myocardium (muscle of the heart) and the pericardium (the outer covering sac of the heart). In this condition, blood or fluid collects within the pericardium and this prevents the ventricles from expanding fully, so they cannot adequately fill up or pump blood. Cardiac tamponade is an emergency condition that usually requires hospitalisation. Treatment is usually accomplished by draining the fluid from around the heart. A further example of a condition treated by aspiration is ascites, which is the accumulation of fluid in the peritoneal (abdominal) cavity. In severe cases the accumulation of up to 25 liters of fluid is fully possible. As previously mentioned, the treatment of all the above conditions essentially comprises of making an incision in the appropriate area of the body and inserting a catheter or cannula to provide a fluid passage through which the excess gas or liquid can be vented or drained.

In the emergency arena the correct diagnosis of the relevant condition is not always guaranteed. Consequently, it would be advantageous to be able to selectively close the open end of the cannula or catheter to prevent the unwanted passage of fluid therethrough, either into or out of the body. Where the condition is correctly identified it would also be advantageous for the excess fluid to be able to vented or drained from the body cavity as required without continued supervision or intervention by a medical practitioner, so that the medical practitioner can turn their attention to either treating other injuries or symptoms or simply conveying the patient to hospital. Additionally, once a catheter, cannula or other appropriate device has been inserted into the patient's body it is desirable for the device or apparatus to remain in the patient's body until the condition has been fully treated. This may require the apparatus to remain located within the patient's body for a considerable period of time. During this time period there is real possibility that either the cannula or catheter, or other fluid passageways within the apparatus, may become wholly or partially blocked by bodily secretions. It is therefore also desirable to be able to actively flush through selected elements of the apparatus to clear these unwanted blockages.

According to a first aspect of the present invention there is provided apparatus for the aspiration of a fluid from an individual, the apparatus comprising a port in fluid communication with the atmosphere, a catheter having a proximal end arranged to be inserted into the body of an individual and having a distal end, a one-way valve and a fluid passage switch reversibly movable between a first position in which the distal end of the catheter is in fluid communication with port and a second position in which the distal end of the catheter is in exclusive fluid communication with the one-way valve, the one-way valve being arranged to permit fluid flow therethrough in a direction from the distal end of the catheter.

It is to be noted that throughout this specification the term "proximal" refers to that part of the apparatus that is closest to the centre of the individual's body when in use.

In preferred embodiments, the fluid passage switch is reversibly movable to a third position in which the one-way valve is in exclusive fluid communication with the port.

Preferably, when the fluid passage switch is in the first position the port and the catheter are axially aligned. This allows a hollow needle to be passed directly through the port and catheter to allow the apparatus to be placed in position within the individual's body.

Advantageously, the port may be arranged to receive a syringe tip therein in a fluid tight manner. This allows either the catheter or one-way valve, depending upon the position of the fluid passage switch, to be flushed with liquid conveyed in the syringe. Equally, it allows manual aspiration to be performed using a syringe, i.e. the syringe is used to extract fluid from the body through the catheter.

In preferred embodiments the one-way valve is arranged to permit fluid flow therethrough whenever there is a pressure differential of at least a predetermined value across the valve. To this end, the one-way valve may comprise a flutter valve.

Additionally or alternatively, the proximal end of the catheter may include a portion of increased resilience in comparison with the remainder of the catheter. This is to help prevent damage of the internal body tissues by the proximal end of the catheter.

Additionally or alternatively, the catheter may have at least one aperture formed therein, the aperture being located between the proximal and distal ends. Preferably there are a plurality of such apertures. The provision of one or more apertures other then the free, proximal end of the catheter, allows aspiration of fluid through the catheter when in use even if the proximal end of the catheter is blocked by internal body tissue.

Additionally or alternatively a portion of the catheter at the distal end thereof may be substantially rigid. The rigidity at the distal end of the catheter helps to prevent buckling or kinking and subsequent constriction of the catheter, which would restrict or prohibit the through flow of fluid through the catheter. Preferably, the resilience of the catheter increases from the distal end to the proximal end. This may be achieved in some embodiments of the present invention by the catheter comprising a side wall having a thickness that decreases from the distal end to the proximal end, i.e. the thickness of the side wall tapers towards the proximal end.

In preferred embodiments, the apparatus further comprises an adhesive element arranged to adhere the apparatus to the skin of the individual. This is to facilitate the quick and easy fixation of the apparatus to the patient's skin in an emergency situation.

Additionally or alternatively, the apparatus may further comprise a body portion having at least one anchor element formed thereon, the anchor element being arranged to receive a securing element for securing apparatus to the skin of the individual. Preferably, the or each anchor element comprises an aperture formed in the body portion, the or each aperture being arranged to receive a suture therethrough and/or a safety pin. The anchor element provides an additional or alternative means of fixation of the apparatus to the skin of the patient.

The one-way valve may be located within a valve housing, the valve housing comprising a connector element. The connector element preferably comprises a Luer connector. This provides a standard means of connecting additional apparatus, such as a syringe or tubing, to the one-way valve, for example, for the positive aspiration of fluid therethrough.

In some embodiments of the present invention the fluid passage switch may be rotatably translatable between the previously mentioned positions, whilst in alternative embodiments the fluid passage switch is linearly translatable between the positions.

Embodiments of the present invention are described below, by way of illustrative example only, with reference to the accompanying figures of which.

Figure 1:
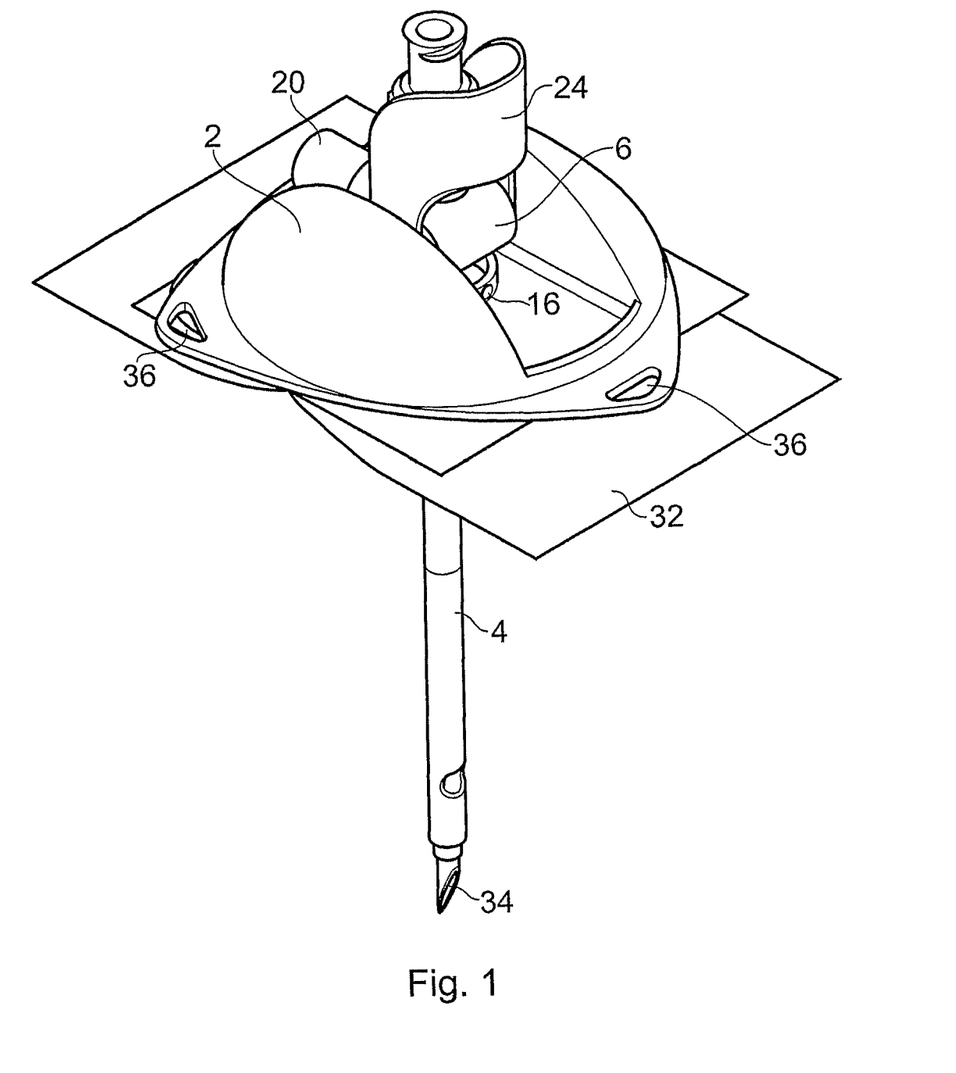
FIG. 1 is a perspective view of a first embodiment of the present invention in combination with a needle prior to use.
Figure 2:
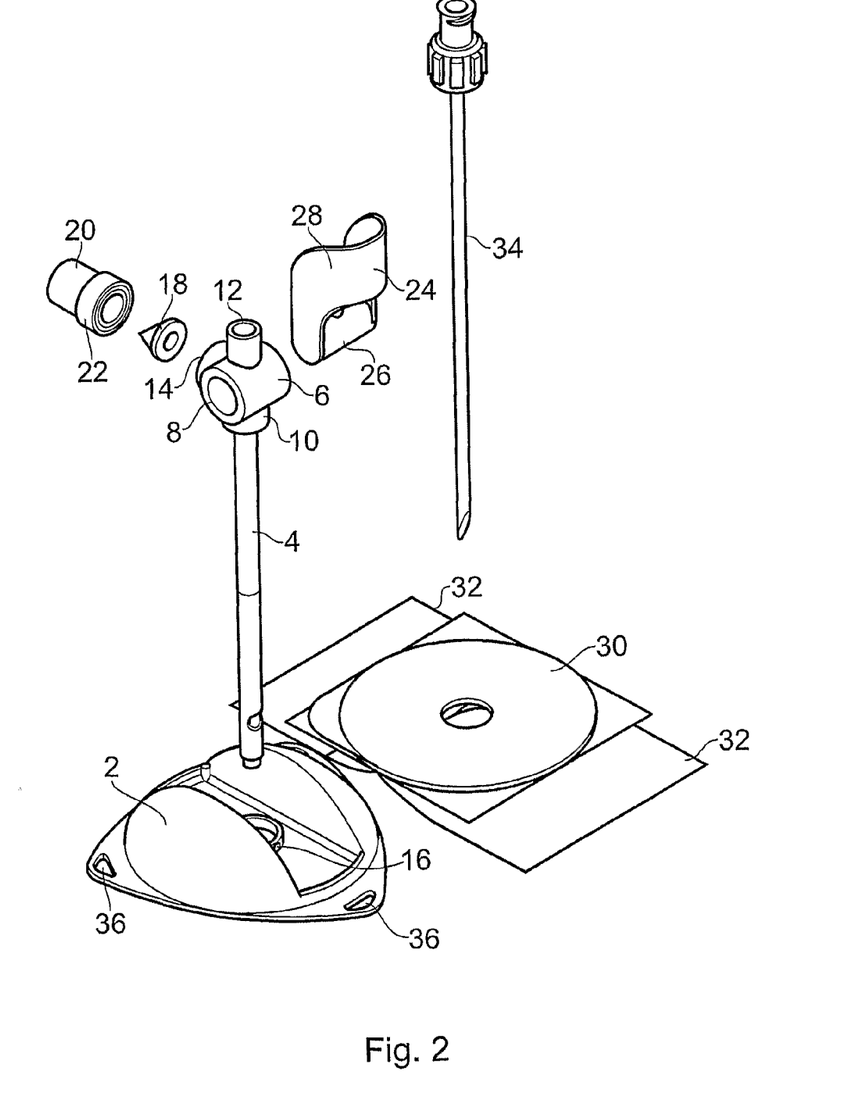
FIG. 2 is an exploded diagram of the apparatus shown in FIG. 1.

FIG. 1 illustrates a perspective view of a first embodiment of the present invention in combination with a needle such that the combination of apparatus and needle is in a condition ready for use. FIG. 2 shows an exploded diagram of the component elements of the apparatus of the first embodiment shown in FIG. 1. The apparatus comprises a main body 2 having a substantially flat lower surface. A catheter 4 extends from the lower surface of the main body and in the embodiment illustrated extends at 90° with respect to the lower side of the main body, although this angle may differ in other embodiments. The distal end of the catheter is mounted within a fluid passage housing 6. The fluid passage housing is in the form of a hollow cylinder 8 with three separate fluid passages extending from the outer side wall of the hollow cylinder, each fluid passage being in fluid communication with the internal bore of the hollow cylinder 8. The distal end of the catheter 4 is located within a first fluid passage 10, with a second fluid passage 12 being axially aligned to the first fluid passage 10 on the opposing side of the hollow cylinder 8. A third fluid passage 14 is orientated at substantially 90° to the first and second fluid passages. The distal end of the catheter and first fluid passage 10 are mounted within a correspondingly shaped orifice within the lower surface of the main body 2. The orifice has an upstanding flange 16 into which the first fluid passage 10 is located. A one-way valve 18 is located within a valve connector 20, which has a substantially cylindrical main body with a fixing collar 22 formed around one end of the connector 20, such that the fixing collar 22 and connector body are co-axially aligned and define an annular recess therebetween. The one-way valve 18 has a circular flange that abuts against the end face of the third fluid passage 14 and is held in place by the valve connector 20. The connector 20 fits over the side wall of the third fluid passage 14, such that the fluid passage 14 is located within the annular recess formed between the connector 20 and the retaining collar 22, the one-way valve 18 being thus restrained between the connector 20 and third passage 14.

A fluid passage switch 24 is provided and comprises a substantially cylindrical body 26 that is housed within the hollow cylinder 8 of the fluid passage housing 6. The main body 26 includes a number of fluid passageways that provide fluid communication between the catheter 4, one-way valve 18 and second fluid passage 12, which will be explained in more detail with reference to FIGS. 3A-3C. The fluid passage switch 24 also includes an actuating lever 28 provided to enable the manual movement of the fluid passage switch into the various operative positions, as shown in FIGS. 3A-3C.

Located on the lower surface of the main body 2 is an adhesive pad 30, which is preferably double sided such that one side of the adhesive pad is securely fastened to the lower surface of the main body 2. The adhesive pad 30 has a corresponding aperture formed therein that is aligned with the aperture in the lower surface of the main body 2. Prior to use, and as shown in FIGS. 1 and 2, one or more peelable cover sheets 32 are provided that are arranged to be removed immediately prior to use to expose the second adhesive surface of adhesive pad 30. In preferred embodiments, and as shown in FIGS. 1 and 2, two separate peelable sheets 32 are provided such that each sheet can be easily peeled away from the distal end of the catheter 4, which would otherwise provide a hindrance in the removal of a single sheet.

Figure 3A:
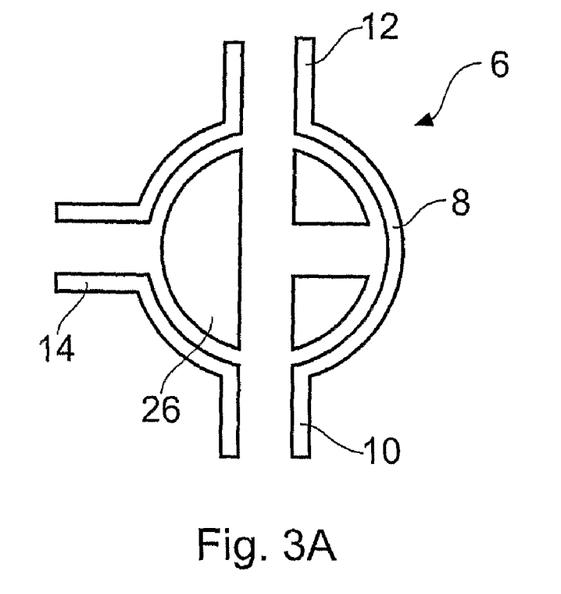
FIGS. 3A-3C are schematic cross-section views of the fluid passage switch and housing of the embodiment shown in FIGS. 1 and 2 with the fluid passage switch in respective different positions.
Figure 3B:
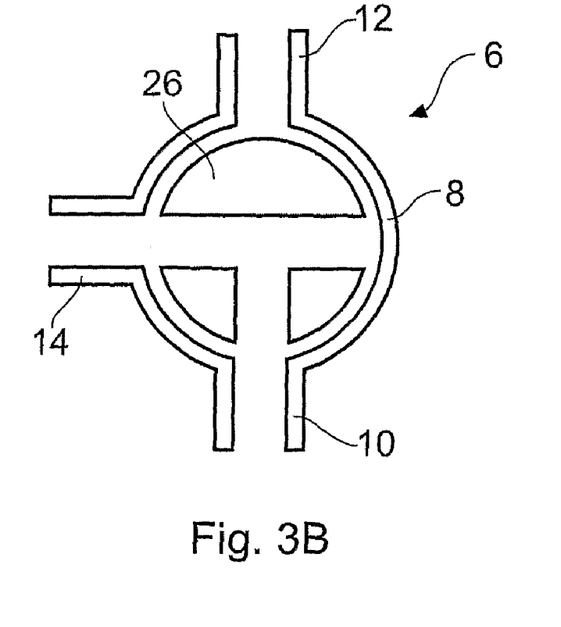
Figure 3C:
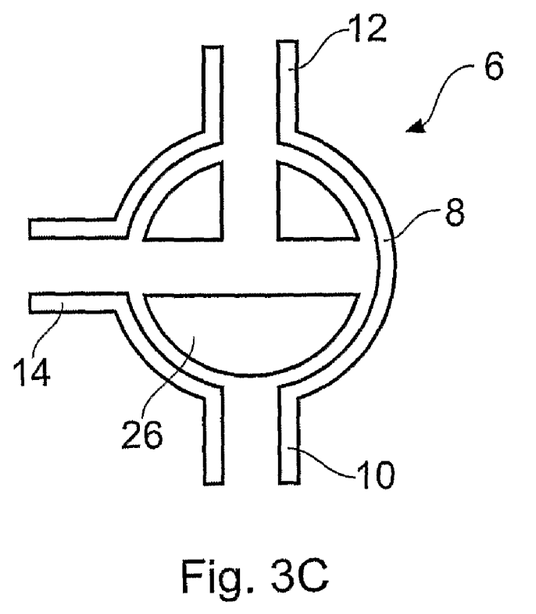

With reference to FIGS. 3A-3C, the fluid passage switch 24 is arranged to be reversibly movable between three main operating positions. The first operating position is illustrated in FIG. 3A, which shows a cross-section through the fluid passage housing 6 and the main body 26 of the fluid passage switch 24. As can be seen from FIG. 3A, the main body 26 of the fluid passage switch has a T-shaped fluid passage formed therein. In the first position, in which the operating lever 28 is preferably axially aligned with the catheter 4, as illustrated in FIG. 1, the first fluid passageway 10, to which the distal end of the catheter 4 is attached, is in exclusive fluid communication with the second fluid passageway 12, which is axially opposite, the third fluid passageway 14 being blocked by the body of the main body 26. It will be appreciated that the main body 26 and the fluid passage housing 6 form a fluid tight seal between one another and that the apparent gap between the housing 8 and main body 26 shown in FIGS. 3A-3D is purely for purposes of clarity of the illustration. The axial alignment between the first and second fluid passageways permits a needle 34 to be passed through the fluid passage switch 6 and the catheter 4. In use, this arrangement of the apparatus and a needle 34 is used to insert the catheter 4 within the relevant body cavity of the individual requiring aspiration, the needle 34 providing the necessary rigidity and, where desired, the sharp point necessary to puncture the intervening skin and tissues. It will be appreciated that the kind of needle used is a free choice, the desirable attribute of the needle being that it is hollow to provide the indication that the desired body cavity has been reached. For example a Verres needle may be selected for use. By using a hollow needle it is possible to determine when the desired body cavity has been reached since the excess fluid is likely to immediately flow through the needle 34. Alternatively, conventional electrical, mechanical or chemical sensors such as, for example, visual indicators or micro electrical-mechanical (MEM) sensors can be used to determine the correct placement of the catheter 4.

The axial alignment of the first and second fluid passages when the fluid passage switch is in the first position indicated in FIG. 3A also permits the catheter to be flushed by means of connecting a syringe, or other source of flushing medium, to the second fluid passage 12. The second fluid passage 12 is therefore preferably provided with a conventional fluid connector, such as a Luer connector.

Once the catheter has been located within the body, the fluid passage switch 24 should be moved into the second position, which is illustrated in FIG. 3B. In the second position the main body 26 of the third passage switch has been rotated by substantially 90° such that only the first fluid passage 10, which is in fluid communication with the catheter 4, and the third fluid passage 14, which is in fluid communication with the one-way valve, are connected, the second fluid passage 12 now being blocked by the main body 26 of the fluid passage switch. In the second position the apparatus provides automatic venting of excess fluid via the one-way valve 18, the valve being arranged to open whenever the fluid pressure within the catheter is greater than that downstream of the one-way valve. It will be appreciated that the one-way valve will operate only when the pressure differential is above a certain minimum value, that minimum value being a function of the construction and materials of the one-way valve.

The fluid passage switch 24 is also arranged to be rotated to a third position, illustrated in FIG. 3C. In this position the main body 26 of the fluid passage switch is rotated substantially 90° from the first position, shown in FIG. 3A, and in the opposite direction of rotation necessary to move the main body from the first to second position. In the third position, the T-shaped fluid passage within the main body 26 of the fluid passage switch provides exclusive fluid communication between the second fluid passage 12, to which a syringe may be connected, and the third fluid passage 14, which is in fluid communication with the one-way valve. In this position it is therefore possible to flush through the one-way valve with a flushing medium provided via a syringe or suitable supply mechanism connected to the second fluid passage 12, yet without passing any of the flushing medium through the catheter 4 into the body cavity of the patient. More importantly, it provides a position in which the catheter 4 is completely sealed. This is important where either the apparatus has been placed within the body of an individual where in fact there is no excessive fluid to be aspirated, or where complete aspiration has taken place and it is therefore necessary to ensure that no outside fluids, such as air, can pass through the catheter 4 from outside the body into the body cavity without removing the apparatus.

Figure 3D:
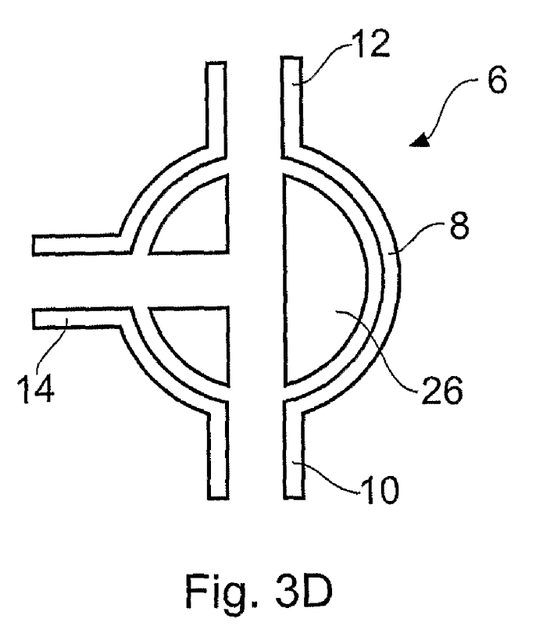
FIG. 3D is a schematic cross-section of an alternative fluid passage switch.

In the preferred embodiment illustrated in FIGS. 3A-3C the arrangement of the T-shaped fluid passage in the main body 26 of the fluid passage switch 24 is such that when the switch is in the second position, in which the catheter and one-way valve are in exclusive fluid communication, the operating lever extends in the opposite direction to the connector 20 of the one-way valve. In an alternative embodiment the T-shaped fluid passage may be orientated at 180° to that shown in FIG. 3A, as is illustrated in FIG. 3D. With this orientation it will be necessary to rotate the lever 28 in the opposite direction to place the switch 24 into the second position, such that the lever is positioned over the one-way valve. Although this is more ergonomically satisfying, since it provides a direct visual indication of the orientation of the fluid passage switch, it results in both the first fluid passage 12 and the third fluid passage 14 being in fluid communication with the first fluid passage 10, and hence the catheter, when the fluid passage switch is in the first position (illustrated in FIG. 3D). This may make it more difficult for a user to determine when the apparatus has been placed in an individual's body correctly.

With reference to FIGS. 1 and 2, the fluid passage switch 24 is arranged such that the actuating lever 28 can pass freely over the free end of the second fluid passage 12 and furthermore is arranged such that the actuating lever 28, when in either the second or third position, lies substantially within the outer profile of the main body 2 of the apparatus. The relatively low profile presented by the apparatus in these positions is advantageous in the emergency scenario since it minimises the likelihood of the apparatus being accidentally caught and dislodged from the patient. Additionally, when the lever is positioned above the one-way valve 18 and connector 20 it affords a degree of physical protection to the connector and valve.

As previously mentioned, the apparatus is preferably provided with an adhesive pad 30 that when the apparatus is in use provides a means for securely adhering the apparatus to the skin of a patient. The adhesive used on the pad 30 is preferably a skin glue, for example, Bioflex® RX416VSA, although other suitable adhesives may also be used. Although such skin glue provides good adhesion between the patient's skin and apparatus even when the skin is wet with moisture or body fluids, the apparatus is preferably provided with further anchor points that enable the main body of the apparatus to be fastened to the patient, either by the use of sutures or the use of safety pins. The anchor points are preferably in the form of one or more apertures 36 formed around the periphery of the main body 2 of the apparatus. The apertures are sized such as to allow either sutures or safety pins to be passed therethrough.

Figure 4:
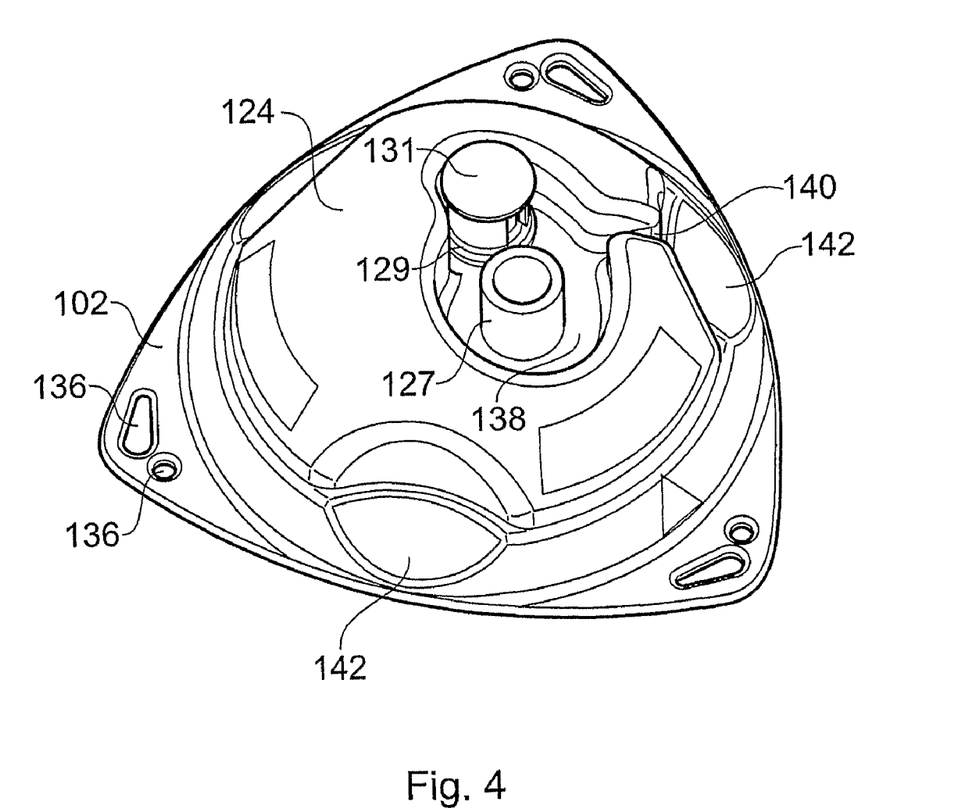
FIG. 4 is a perspective view of the top side of a second embodiment of the present invention.
Figure 5:
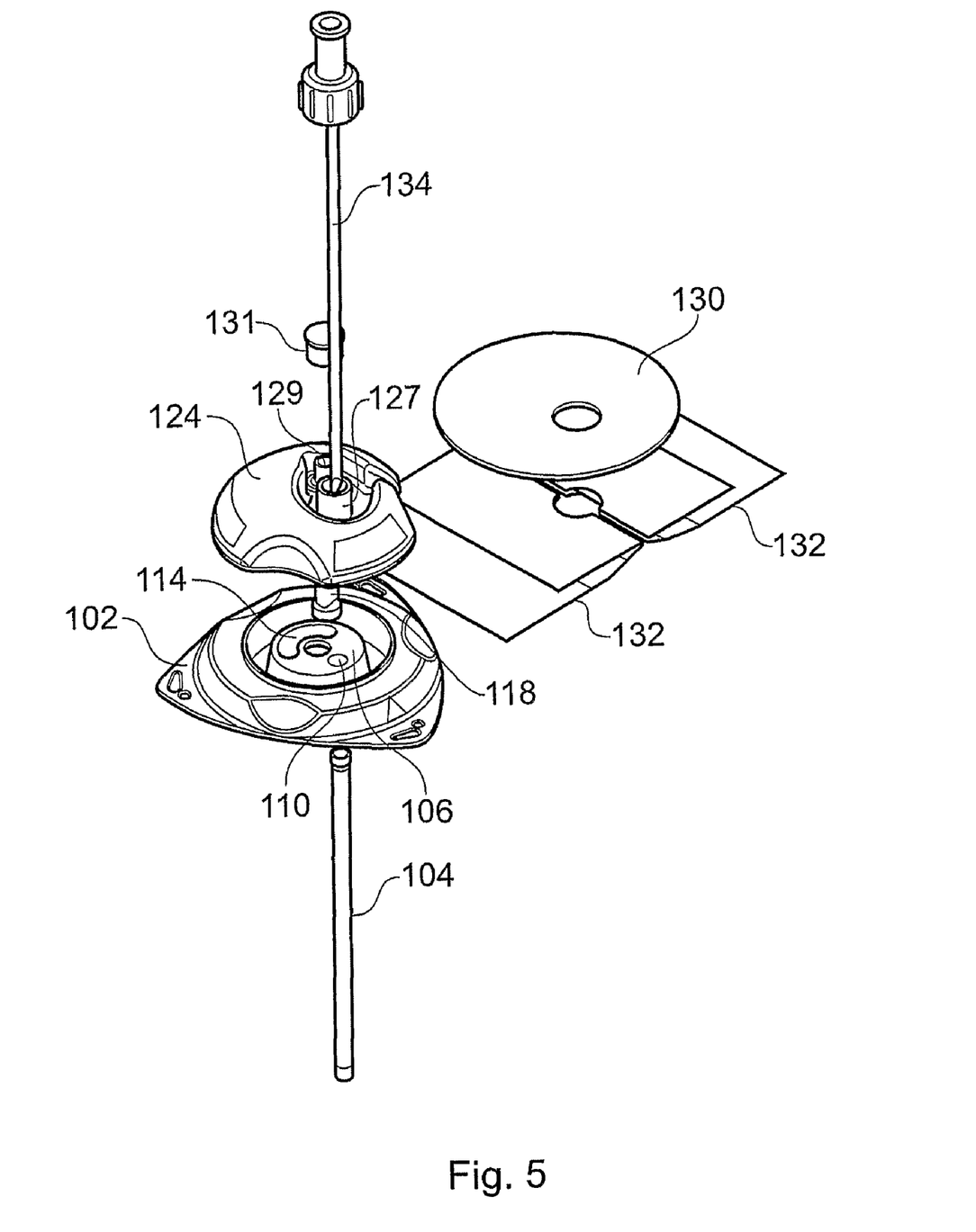
FIG. 5 is an exploded diagram of the elements of the apparatus shown in FIG. 4, with the addition of a needle.

FIGS. 4 and 5 illustrate a second embodiment of the present invention, with FIG. 5 illustrating an exploded diagram of the various elements of the second embodiment. As with the first embodiment, the second embodiment shown in FIGS. 4 and 5 comprises a main body portion 102 having a substantially flat lower surface. However, in the second embodiment the fluid passage housing and fluid passages are integrally formed in the main body portion 102. As shown in FIG. 5, a fluid passage portion 106 is provided integrally with the main body portion 102 in the form of a raised cylindrical section that is preferably axially aligned with the central axis of the apparatus. The fluid passage portion 106 has a first substantially cylindrical fluid passageway 110 formed therein which extends completely through the main body portion 102. A catheter 104 is connected to the first fluid passageway 110 at the distal end of the catheter. The first fluid passageway 110 is offset from the central axis of the apparatus. The fluid passage portion 106 also has a second fluid passage 114 that is in the form of a kidney shaped or arc shaped recess formed in the upper surface of the fluid passage portion 106. A fluid housing switch 124 is mounted to the upper surface of the main body portion 102 so as to enclose the fluid passage portion 106 in a fluid tight manner. The fluid passage switch 124 has first and second ports 127, 129 formed in the upper surface thereof. The first port 127 comprises a simple cylindrical aperture to which a syringe or other fluid supply mechanism may be preferably connected. The first port 127 is dimensioned so as to be able to receive a hollow needle 134 therethrough. The second port 129 has a one-way valve 118 housed therein and preferably is arranged to receive a cap 131.

In a substantially identical manner to the first embodiment, the second embodiment includes an adhesive pad 130 secured to the lower planar surface of the main body portion 102 and having an aperture therein aligned with the first fluid passage 110 of the fluid passage portion 106. Twin adhesive release sheets 132 are also preferably provided.

Figure 6A:
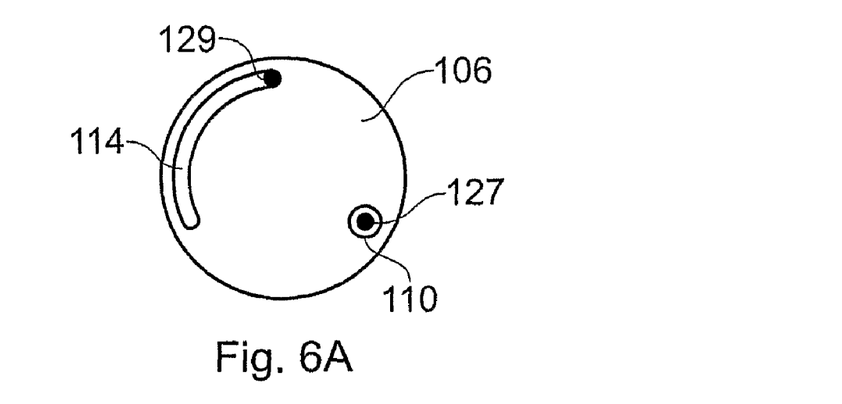
FIGS. 6A-6C schematically illustrate the respective positions of one-way valve and port of the embodiment of the present invention shown in FIGS. 4 and 5.

The fluid passage switch 124 can be rotated with respect to the main body 102 so as to selectively bring the first and second ports 127, 129 into fluid communication with the first fluid passage 110 and/or the second fluid passage 114. FIG. 6A schematically illustrates the first position of the fluid passage switch 124 and in particular the spatial relationship between the first and second ports 127, 129 and the first and second fluid passages 110, 114 located within the fluid passage portion 106. In the first position the first port 127 is in exclusive fluid communication with the first fluid passage 110. Consequently, a needle 134 can be passed directly through the first port 127, first fluid passage 110 and the catheter 104 so that the apparatus can be subsequently inserted within the body of a patient. In this position, the second port 129, which houses the one-way valve 118 is in fluid communication with the second fluid passage 114.

Figure 6B:
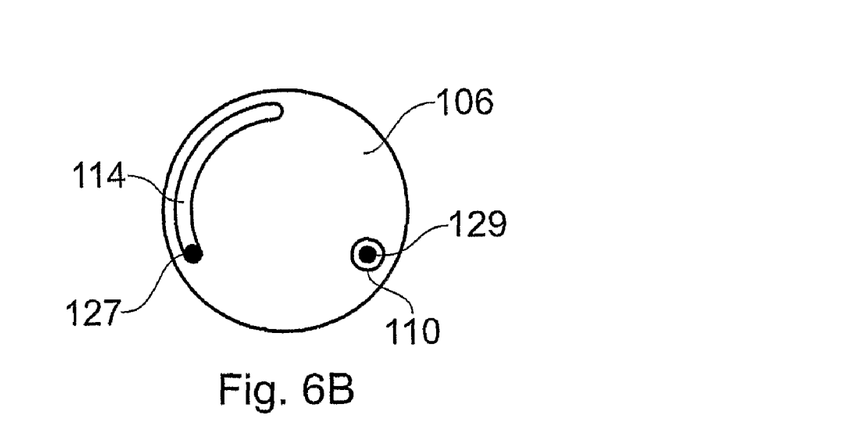

FIG. 6B schematically illustrates the relative positions of the ports and fluid passages when the fluid passage switch 124 has been rotated through 120° clockwise with respect to the first position. In this second position the second port 129 that houses the one-way valve 118 is now in exclusive communication with the first fluid passage 110, which in turn is in communication with the catheter 104. Therefore any excess fluid within the patient's body cavity is free to vent through the one-way valve via the catheter. As previously mentioned, the second port 129 preferably has a cap 131 fitted over it. The cap 131 preferably has at least one opening formed in its side wall such that even with the cap placed over the port it is still possible for fluid to be expelled through the one-way valve via the opening in the side wall of the cap. In the second position, the first port 127 is in communication with the second fluid passage 114. However, since the second passage 114 is a blind recess no further access to the patient's body is provided by the first port 127 in this position.

Figure 6C:
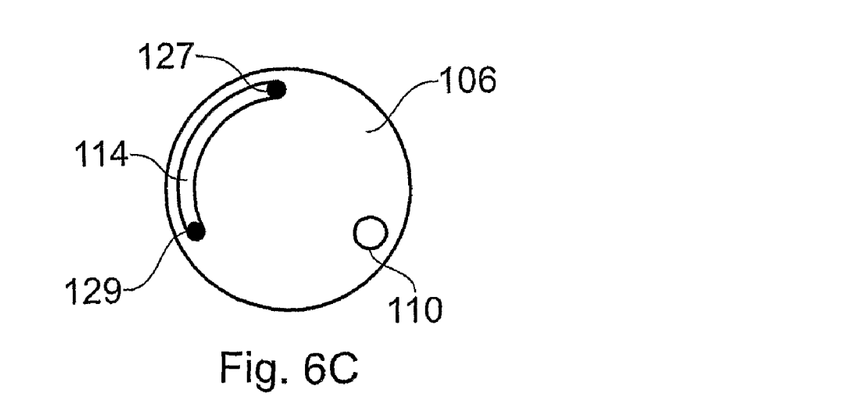

FIG. 6C illustrates the relative positions of the first and second ports and fluid passages when the fluid passage switch 124 has been rotated by a further 120° clockwise. In the third position the first and second ports 127, 129 are in fluid communication with opposite extremities of the second fluid passage 114. Consequently, the first and second ports 127, 129 are in fluid communication with one another. This allows a flushing medium to be introduced into the first port 127 and passed under pressure through the one-way valve 118 and second port 129, so as to clean or unblock the one-way valve of any accumulated body fluids or tissues. Furthermore, in the third position the first fluid passage 110, which is in fluid communication with the catheter 104 and therefore the internal cavity within the patient's body, is sealed in a fluid tight manner by the lower surface of the fluid passage switch 124.

In the embodiment illustrated in FIGS. 4 and 5, the fluid passage switch 124 is formed with a recess in its upper surface in which the first and second ports 127, 129 are located. The recess 138 allows the fluid ports 127, 129 to be recessed within the overall external profile of the fluid passage switch 124 and further provides, in conjunction with a communicating drainage channel 140, the means for any fluids expelled through the one-way valve and second fluid port 129 to be drained away in a controlled direction from the apparatus. The fluid passage switch 124 and the main body portion 102 of the apparatus preferably include correspondingly located indicators, which in the embodiment shown in FIGS. 4 and 5 comprise shallow concave recesses 142 formed in their outer edges and arranged to be aligned with one another when the fluid passage switch 124 is in each of the first, second or third positions, so as to provide a visual and tactile confirmation to a user that the fluid passage switch 124 is correctly orientated in a desired position. Further indicia may be included to aid a person in correctly selecting the desired position of the fluid passage switch, particularly in low light levels such as may be encountered in an emergency scenario. For example, each of the recesses 142 may be differently shaped to indicate the different positions. Luminous indicia may also be provided. The main body portion 102 may also include anchor elements 136 for securing the apparatus to a patient by suturing or pinning. In the embodiment shown in FIGS. 4 and 5, separate apertures are provided for suturing and pinning.

Figure 7:
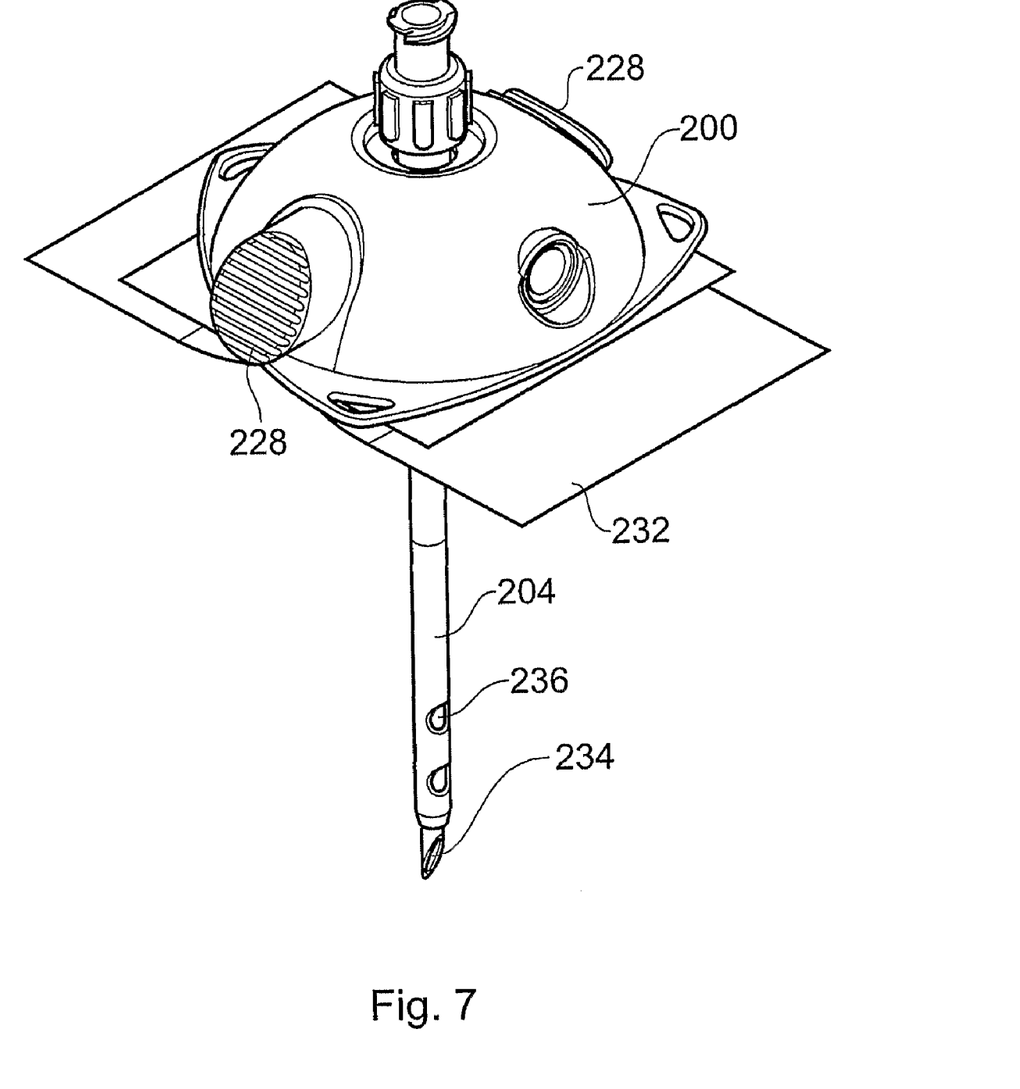
FIG. 7 is a perspective view of a third embodiment of the present invention in combination with a needle prior to use.
Figure 8:
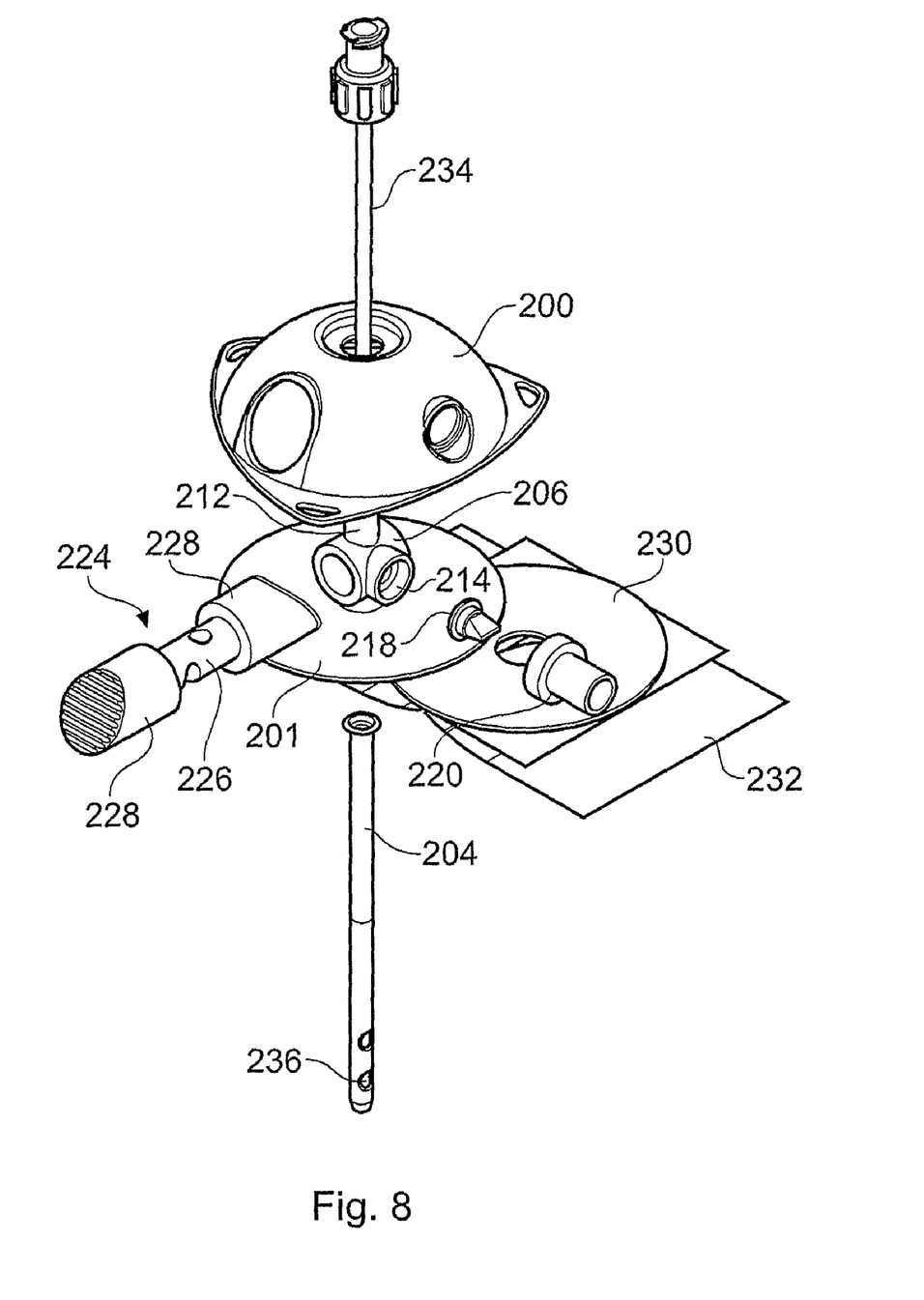
FIG. 8 is an exploded diagram of the elements of the embodiment shown in FIG. 7.

FIGS. 7 and 8 illustrate a third embodiment of the present invention, with FIG. 8 illustrating an exploded view of the separate elements of the third embodiment. In the third embodiment the main body portion comprises an upper, domed, shell 200 and a lower, planar base portion 201. The upper shell 200 and lower base portion 201 fit together and define an internal cavity within the upper shell 200. Housed within the upper shell 200 is a fluid passage housing 206 that is structurally identical to the fluid passage housing 6 illustrated with respect to the first embodiment of the present invention. A first fluid passage of the fluid passage housing is located within a corresponding aperture within the base 201 of the main body portion and also has the distal end of a catheter 204 received therein. A second fluid passage 212 extends from the fluid passage housing 206 in an opposing direction from, and axially aligned with, the first fluid passage and catheter 204. The second fluid passage 212 is also axially aligned therewith an aperture formed in the upper surface of the upper body shell 200. A third fluid passage 214 is provided in the fluid passage housing 206 at substantially 90° to the first and second fluid passages. The third fluid passage 214 includes a flange arranged to receive one end of a one-way valve 218. A fluid connector 220 encloses the opposite end of the one-way valve and forms a fluid tight connection with the third fluid passage 214. The free end of the fluid connector 220 is axially aligned with a second orifice provided in the upper shell 200 of the main body.

A fluid passage switch 224 is also provided. A fluid passage switch 224 has a central portion that forms the fluid passage body 226. The fluid passage body 226 has a number of fluid passages formed therein, which will be described in more detail below. The fluid passage body 226 is arranged to be received within the fluid passage housing 206 in a fluid tight manner but also such that the fluid passage body 226 may be linearly translated within the fluid passage housing 206. The fluid passage body of the switch 224 is therefore necessarily axially longer than the main cylindrical body of the fluid passage housing 206. Mounted at either end of the fluid switch main body 226 are opposing actuating buttons 228. Each actuating button 228 is of greater cross sectional area than the fluid passage body 226, such that each actuating button 228 also acts as a restraint to restrict the linear translation of the fluid passage switch 224 as a whole within the fluid passage housing 206. Each actuating button 228 extends through a correspondingly shaped aperture within the upper shell 200 of the apparatus.

As with the previously described embodiments, an adhesive pad 230 is attached to the base portion 201 of the main body with the catheter 204 extending through a orifice within the adhesive pad. Peel off sheets 232 are also provide to the free surface of the adhesive pad.

As previously mentioned, the central portion of the fluid passage switch 224 has three separate fluid passages formed therein. Each passage is linearly offset from one another by a predetermined distance. In a first position, in which a first one of the actuating buttons 228 of the fluid passage switch 224 abuts against a corresponding side of the fluid passage housing 206, a first of the fluid passages within the central portion of the fluid passage switch 224 enables a fluid communication between, for example, the first and third fluid passages of the fluid passage housing 206, such that the catheter 204 and one-way valve 218 are in exclusive fluid communication with one another. In this position an apparatus which has already been placed within an appropriate body cavity of an individual allows any excess of fluid contained within the body to be expelled through the one-way valve via the catheter. In a second, opposite position, achieved by linearly translating the fluid passage switch 224 to its further extent in the opposite direction from which it occupies in the first position, a second fluid passage provides exclusive fluid communication between the second and third fluid passages, thus providing exclusive fluid communication between the third fluid passage 212, which can be accessed via the orifice in the upper housing 200, and the one-way vent, thus allowing flushing of the event if desired. In a third, intermediary position, a third fluid passage is provided in the fluid passage switch 224 that provides fluid communication between the first and second fluid passages, such that the second fluid passage 212 is axially aligned with the interior of the cavity 204 such that a needle 234 can be passed therethrough. In this position, and with the needle located therein, the apparatus may be inserted into the patients body. As with previously described embodiments tactile and/or visual indicia or other markers may be provided to give an indication to a user that the desired position of the fluid passage switch has been correctly selected.

As with the first and second embodiments, in the third embodiment shown in FIGS. 7 and 8 the main body, in this instance the upper body portion 200, includes anchor apertures which either sutures or safety pins can be passed to enable the apparatus to be additionally secured to the skin of a patient. Also shown in FIGS. 7 and 8 and optionally included in the first and second embodiments, the catheter 204 includes one or more openings 236 in the side walls of the catheters 204, preferably located towards a proximal, free, end of the catheter. These openings allow fluid to flow into the catheter 204 even if the free end of the catheter is blocked by, for example, body tissue. In preferred embodiments, the catheter increases in flexibility and resilience towards the proximal end, such that the proximal end of the catheter is flexible enough to substantially avoid damage to surrounding body tissue, but is sufficiently rigid at the distal end, i.e. towards the body of the apparatus, to prevent buckling or kinking and subsequent constriction of fluid flow therethrough. This can be achieved through the catheter consisting of different materials with appropriate properties along its length or by varying its cross-section, for example such that the cross-section of the side walls of the catheter are tapered with the thinnest portion being towards the proximal end of the catheter. In certain embodiments the catheter may also feature a pre-applied bend at the proximal end to reduce the risk of tissue damage otherwise caused by a straight catheter.

Although the three embodiments illustrated in the accompanying Figures illustrate the catheter being substantially 90° to the main body portion of the apparatus, it will be appreciated that other angles may be adopted without significant deviation from the current invention where the particular application so demands this modification.

As mentioned in the introductory part of the description, the most common procedure in which the apparatus of the present invention may be used to provide treatment is a tension pneumothorax. However other procedures could include pericardiocentesis (cardiac tamponade), pleural aspiration (pleural effusion), abdominal aspiration (abdominal effusion e.g. ascites), placement of suprapubic catheters, joint aspiration, spinal aspiration, installation of fluid (sclerosis of the pleural space in malignancy), or any other kind of sterile liquid sample extraction. However, the method of operation remains substantially the same, namely that the fluid passage switch is placed into a first position in which a hollow needle can be passed through the main body of the apparatus and through the interior of the catheter, the needle protruding beyond the proximal end of the catheter. The device is then inserted into the appropriate position within the patients body, the needle providing the sufficient rigidity and cutting function to penetrate the patients skin and tissue. The needle is then withdrawn and the fluid passage switch moved to a second position, in which the catheter and one-way valve are in exclusive fluidic communication with one another, such that fluid located within the body cavity in which the catheter has been introduced can be expelled through the one-way valve. Ordinarily, the fluid will be at a pressure greater than atmospheric pressure such that aspiration occurs automatically. However, a syringe or other suction device may be attached to the one-way valve port and the fluid positively removed. If it is desired to seal the catheter and/or flush the one-way valve the fluid passage switch is moved to a third position in which the one-way valve and second external port are in exclusive fluid communication with one another, the catheter being sealed. A syringe, or other source of flushing medium, may then be connected to the second port such that the flushing medium can be passed through the one-way valve.

In some medical procedures it may be desirable to perform positive aspiration in which fluid is repeatedly withdrawn from the body using, for example, a syringe. To facilitate this process further embodiments of the invention may be provided in which either the one-way valve 18 is replaced with a two-way valve or a further one-way valve is provided. For example, in the embodiment of the fluid passage switch illustrated in FIG. 3D a further one-way valve may be located in the first fluid passageway 10 arranged to allow fluid flow out of the body through the catheter only. A syringe may then be connected to the fluid passageway 12 to extract fluid through the catheter and expel the fluid through the third passageway 14. Alternatively, a two-way valve may be located in the catheter itself, in which case the one-way valve located in the third fluid passageway 14, the third fluid passageway being retained to allow fluid to be expelled under positive aspiration as explained above. In such embodiments it may be necessary to preassemble the apparatus with a needle inserted through the relevant one-way or two-way valves.

In certain medical procedures it may be necessary to introduce fluid into the body (instillation). This can be easily accomplished using embodiments of the present invention by positioning the fluid passage switch into the first position, in which the second fluid passageway is in fluid communication with the catheter, connecting a syringe or other source of fluid to be instilled into the body and passing the fluid through the catheter into the body.

The invention claimed is:

1. Apparatus for providing a fluid passageway into an individual, the apparatus comprising:
 a port in fluid communication with the atmosphere;
 a catheter having a proximal end arranged to be inserted into the body of an individual and having a distal end;
 a one-way valve; and
 a fluid passage switch, in fluid communication with the port, catheter and one-way valve, wherein:
 the one-way valve is arranged to only permit the aspiration of fluid out of the apparatus;
 the fluid passage switch and the port are arranged to receive a needle therein; and
 the fluid passage switch is reversibly movable between a first position in which the distal end of the catheter is in fluid communication with the port and in which the port and the catheter are axially aligned, such that whenever the fluid passage switch is in the first position a needle can be introduced into the catheter via the port and fluid passage switch, and a second position in which the distal end of the catheter is in fluid communication with the one-way valve, such that whenever the fluid passage switch is in the second position aspiration of fluid through the catheter and subsequently the one-way valve is permitted.

2. The apparatus of claim 1, wherein in the first position the catheter and the port are in exclusive fluid communication with one another.

3. The apparatus of claim 1 wherein in the second position the catheter and the one-way valve are in exclusive fluid communication with one another.

4. The apparatus of claim 1 wherein the fluid passage switch is reversibly movable to a third position in which the one-way valve is in exclusive fluid communication with the port.

5. The apparatus of claim 1 wherein the port is arranged to receive a syringe tip therein in a fluid tight manner.

6. The apparatus of claim 1 wherein the one-way valve is arranged to permit fluid flow therethrough whenever there is a pressure differential of at least a predetermined value across the valve.

7. The apparatus of claim 1 wherein the one-way valve comprises a flutter valve.

8. The apparatus of claim 1 wherein the proximal end of the catheter includes a portion of increased resilience in comparison with the remainder of the catheter.

9. The apparatus of claim 1 wherein the catheter has at least one aperture (236) formed therein, the aperture being located between the proximal and distal ends.

10. The apparatus of claim 8, wherein the catheter has a plurality of apertures (236) formed therein, each aperture being located between the proximal and distal ends.

11. The apparatus of claim 8 or 9, wherein the or each aperture (236) is located closer to the proximal end of the catheter than to the distal end.

12. The apparatus of claim 1 wherein a portion of the catheter at the distal end thereof is substantially rigid.

13. The apparatus of claim 1 wherein the resilience of the catheter increases from the distal end to the proximal end.

14. The apparatus of claim 12, wherein the catheter comprises a side wall having a thickness that decreases from the distal to the proximal end.

15. The apparatus of claim 1 further comprising an adhesive element arranged to adhere the apparatus to the skin of the individual.

16. The apparatus of claim 1 further comprising a body portion having at least one anchor element formed therein, the anchor element being arranged to receive a securing element for securing the apparatus to the skin of the individual.

17. The apparatus of claim 15, wherein the or each anchor element comprises an aperture formed in the body portion, the or each aperture being arranged to receive a suture therethrough.

18. The apparatus of claim 16, wherein the or each aperture is arranged to receive a safety pin therethrough.

19. The apparatus of claim 1 wherein the one-way valve is located within a valve housing, the valve housing comprising a connector element (20).

20. The apparatus of claim 18, wherein the connector element comprises a Luer connector.

21. The apparatus of claim 1 wherein the fluid passage switch is rotatably translatable between said positions.

22. The apparatus of claim 1 wherein the fluid passage switch is linearly translatable between said positions.

23. A method of providing a fluid passageway into the body of an individual utilising an apparatus in accordance with claim 1, the method comprising:
 positioning the fluid passage switch in the first position and introducing a needle into the catheter via the port;
 introducing the needle and catheter into a body cavity within the individual;
 removing the needle; and
 positioning the fluid passage switch into the second position.

24. The method of claim 23, further comprising the subsequent steps of re-positioning the fluid passage switch into the first position and introducing an external fluid into the catheter via the port.

25. The method of claim 23, wherein the external fluid is introduced into the body cavity.

26. The method of claim 23, further comprising re-positioning the fluid switch into a third position in which the one-way valve is in exclusive fluid communication with the port and passing a flushing medium from the port through the one-way valve.

27. The method of claim 23, further comprising applying a negative pressure source to the one-way valve.

28. The method of claim 23, further comprising applying negative pressure to the port to withdraw a portion of fluid from body cavity via the catheter and subsequently expelling the withdrawn fluid via the one-way valve.

* * * * *